United States Patent [19]

Gross

[11] Patent Number: Plant 7,752

[45] Date of Patent: Dec. 17, 1991

[54] POINSETTIA NAMED GROJI

[76] Inventor: Bruno Gross, "Le Bois" Angeac Champagne 16130 Segonzac, 16130 Segonzac Charente, France

[21] Appl. No.: 466,883

[22] Filed: Dec. 6, 1989

[51] Int. Cl.[5] ..... A01H 5/00

[52] U.S. Cl. ..... Plt./86

[58] Field of Search ..... Plt./86

[56] References Cited

U.S. PATENT DOCUMENTS

P.P. 6,592 2/1989 Gross ..... Plt. 86

*Primary Examiner*—James R. Feyrer

*Attorney, Agent, or Firm*—Jordan and Hamburg

[57] ABSTRACT

A new Poinsettia cultivar distinguished by large, bright red bracts, small leaves with very deep incisions and a short growth habit is herein described. The stems of this plant have short internodes, yet possess a strong self-branching habit. As a flowering potted plant, it performs equally well as a single-stemmed, unpinched plant or a branched, pinched plant.

1 Drawing Sheet

BACKGROUND OF THE NEW PLANT

This new Poinsettia originated as a seedling and was produced by me in my greenhouse in Le Bois d'Angeac, France. I selected this plant because of its large bright red bracts, distinctively shaped green leaves, short growth habit, strong stems and self-branching characteristics. This new Poinsettia flowers equally well as either a pinched, multiple branched plant or as an unpinched single stem plant. The plant's characteristics are unique, resulting in a plant which is recognizable as being different from any other Poinsettia cultivar. I propagated this new plant by vegetative cuttings through successive generations, which time and again has shown its strong stems and distinctively shaped leaves, short stature and bright red bracts which have remained unchanged from generation to generation.

DESCRIPTION OF THE DRAWING

My new variety of Poinsettia is illustrated by the accompanying full color photographic drawing, the color being as true to that herein specified as is reasonably possible to obtain by conventional photographic procedures.

DESCRIPTION OF THE NEW PLANT

The following is a detailed description of this new Poinsettia as observed under greenhouse culture in Le Bois d'Angeac, France. Color designations are according to The R.H.S. Colour Chart published in 1966 by The Royal Horticultural Society at London, England.

THE PLANT

Origin: Cross breeding of our own variety Grotifer-×our own variety No. 2J.

Classification:

*Botanic.*—*Euphorbia pulcherrima.*

Form: Shrub.

Height: Typically 80 cm after one year.

Growth habit: As a single stem, upright, but short. The leaves are unusually very deeply incised. The stems are strong with closely spaced nodes. I observed flowering stems of 20–22 cm length with red bract presentations 18–20 cm in diameter.

Branching: Upright with many stems producing a compact, bushy plant full in appearance.

Growth rate: Very fast. No growth regulator is needed. Rooting of vegetative cuttings occurs in 15–20 days under intermittent mist and the plant will flower in about 8 weeks under continuous long night conditions and night temperatures of 16°–18° C. The plant breaks out with many branches and gives more cuttings than the other known varieties. There are many shooting lateral buds after pinching.

Foliage: This plant has unusual small, very deeply incised, erect leaves having a dark green upper side and a light green underside, with the plane of the leaf blade nearly perpendicular to the stem. There is no leaf torsion. The leaves have no hair. The larger leaves typically have leaf blades 10–12 cm long and 4–7 cm wide and leaf petioles 3–4 cm long. The color of the petiole surface is reddish.

Leaf shape: Typical mature leaves are lanceolate in overall shape, the apex of a mature leaf being acuminate in shape and the base thereof being acute in shape. The leaf margins have very deep incisions. Torsion is absent in the mature leaf.

Bracts: Generally there are 10–12 uniformly colored bright red bracts, typically thicker and larger than most Poinsettia cultivars. Bract color is very stable. It is not unusual for the larger bract-leaf blades to be 10–13 cm long and 9–12 cm wide with short leaf petioles, 2–4 cm long, which are reddish in color. The short bract petioles result in a bract presentation with a close, tight center.

Shape: In overall shape, the bracts are usually ovate with a medium degree of incisions on their margins and have an acute apex and an acute base.

Color:

*Upper side.*—RHS 53B near the border and 45A in the middle.

*Under side.*—RHS 46B/C.

The cyathia are medium size and have two to six nectar cups. The coloration of the cyathia is yellow-orange. The stigma are red.

I claim:

1. A new and distinctive Poinsettia cultivar, substantially as herein shown and described, particularly distinguished by large, bright red bracts, strong stems and small leaves with very deep incisions and a short, self-branching growth habit.

* * * * *

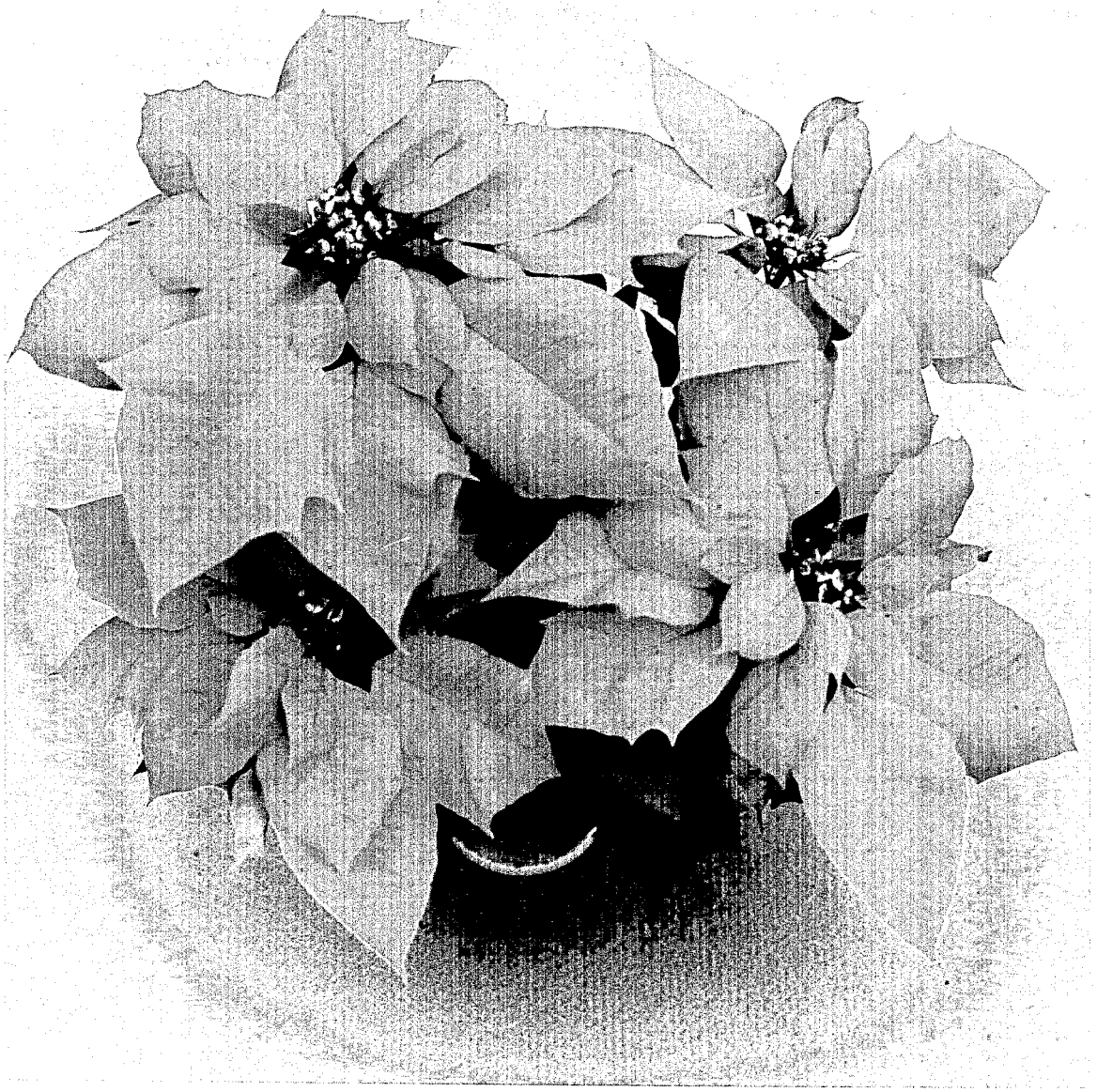

UNITED STATES PATENT AND TRADEMARK OFFICE

CERTIFICATE OF CORRECTION

PATENT NO. : Plant 7,752

DATED : December 17, 1991

INVENTOR(S) : Bruno GROSS

It is certified that error appears in the above-identified patent and that said Letters Patent is hereby corrected as shown below:

On the title page:

Item 21, Appl. No., change "466,883" to --446,883--.

Signed and Sealed this

Seventeenth Day of March, 1992

*Attest:*

HARRY F. MANBECK, JR.

*Attesting Officer*

*Commissioner of Patents and Trademarks*